(12) United States Patent
Cole

(10) Patent No.: US 8,269,639 B2
(45) Date of Patent: Sep. 18, 2012

(54) PARTICLE MONITORS AND METHOD(S) THEREFOR

(75) Inventor: Martin Terence Cole, Patterson Lakes (AU)

(73) Assignee: Siemens Schweiz AG, Zurich (CH)

( * ) Notice: Subject to any disclaimer, the term of this patent is extended or adjusted under 35 U.S.C. 154(b) by 601 days.

(21) Appl. No.: 12/440,477

(22) PCT Filed: Sep. 7, 2007

(86) PCT No.: PCT/AU2007/001313
§ 371 (c)(1),
(2), (4) Date: May 13, 2009

(87) PCT Pub. No.: WO2008/064396
PCT Pub. Date: Jun. 5, 2008

(65) Prior Publication Data
US 2010/0039274 A1    Feb. 18, 2010

(30) Foreign Application Priority Data

Sep. 7, 2006    (AU) .............................. 2006904899

(51) Int. Cl.
*G08B 21/00*    (2006.01)
*G01N 21/00*    (2006.01)
*C12Q 1/04*    (2006.01)

(52) U.S. Cl. ........ 340/627; 340/618; 340/619; 356/432; 356/436; 435/34

(58) Field of Classification Search ............... 340/612, 340/618, 619, 627, 628, 630; 356/39, 73, 356/336, 432; 349/14, 193; 399/53, 57, 223; 438/708; 435/34

See application file for complete search history.

(56) References Cited

U.S. PATENT DOCUMENTS

| | | | |
|---|---|---|---|
| 3,982,130 A | 9/1976 | Trumble | |
| 4,011,458 A | 3/1977 | Malinowski et al. | |
| 4,206,456 A | 6/1980 | Malinowski et al. | |
| 4,906,978 A | 3/1990 | Best et al. | |
| 5,194,921 A * | 3/1993 | Tambo et al. | 356/432 |
| 5,899,605 A * | 5/1999 | Caruthers et al. | 399/223 |
| 6,011,478 A | 1/2000 | Suzuki et al. | |
| 6,069,687 A * | 5/2000 | Briggs | 356/39 |
| 6,377,345 B1 * | 4/2002 | Powell | 356/336 |
| 6,797,959 B2 | 9/2004 | Chang et al. | |
| 7,508,313 B2 | 3/2009 | Cole | |
| 7,551,277 B2 | 6/2009 | Cole | |
| 2002/0182877 A1 * | 12/2002 | Nantel et al. | 438/708 |
| 2005/0000531 A1 * | 1/2005 | Shi | 131/347 |
| 2007/0020721 A1 * | 1/2007 | Yoshida et al. | 435/34 |

FOREIGN PATENT DOCUMENTS

EP    0877345 A2    11/1998

(Continued)

*Primary Examiner* — Van T. Trieu
(74) *Attorney, Agent, or Firm* — Laurence A. Greenberg; Werner H. Stemer; Ralph E. Locher

(57) ABSTRACT

The present invention relates to the field of the detection, analysis and/or determination of matter or particles suspended in fluid. In one particular form, the present invention relates to smoke detectors, which detect unwanted pyrolysis or combustion of material. In another form, the present invention relates to smoke detectors of the early detection type, and which may be applied to ventilation, air-conditioning or duct monitoring of a particular area. In yet another form, the present invention relates to adjusting the sensitivity of particle detectors.

19 Claims, 2 Drawing Sheets

FOREIGN PATENT DOCUMENTS

| | | |
|---|---|---|
| GB | 2267963 A | 12/1993 |
| GB | 2319605 A | 5/1998 |
| JP | 1074695 A | 3/1989 |
| JP | 6109631 A | 4/1994 |
| WO | 0159737 A1 | 8/2001 |
| WO | 2005043479 A1 | 5/2005 |

* cited by examiner

FIG. 3
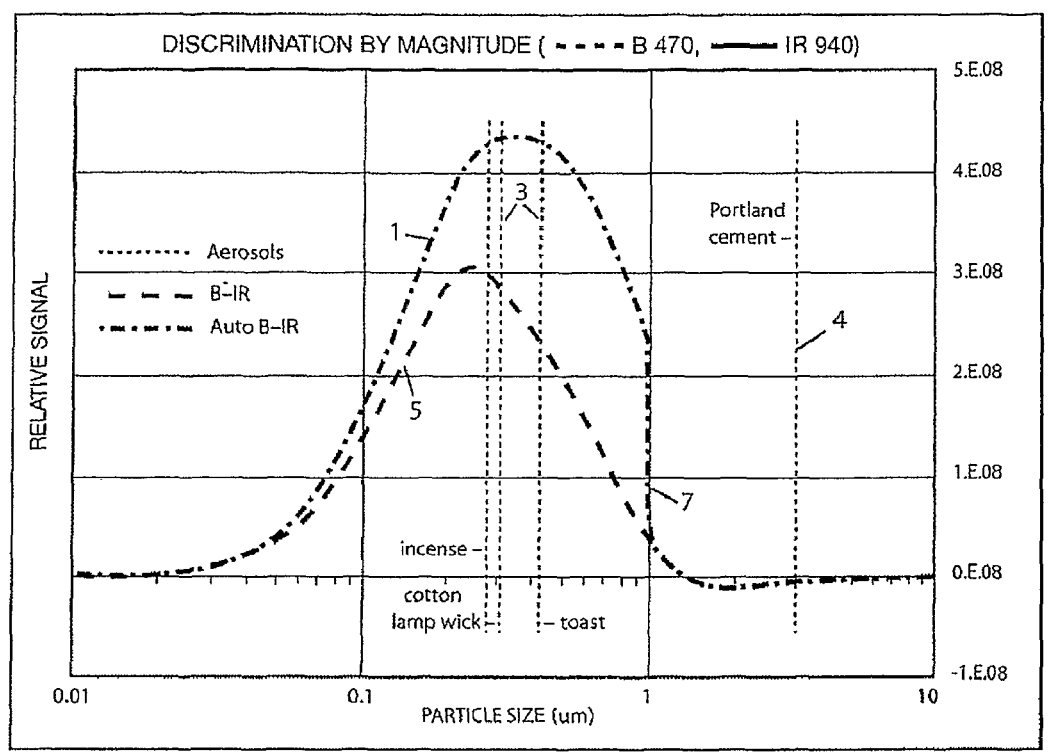
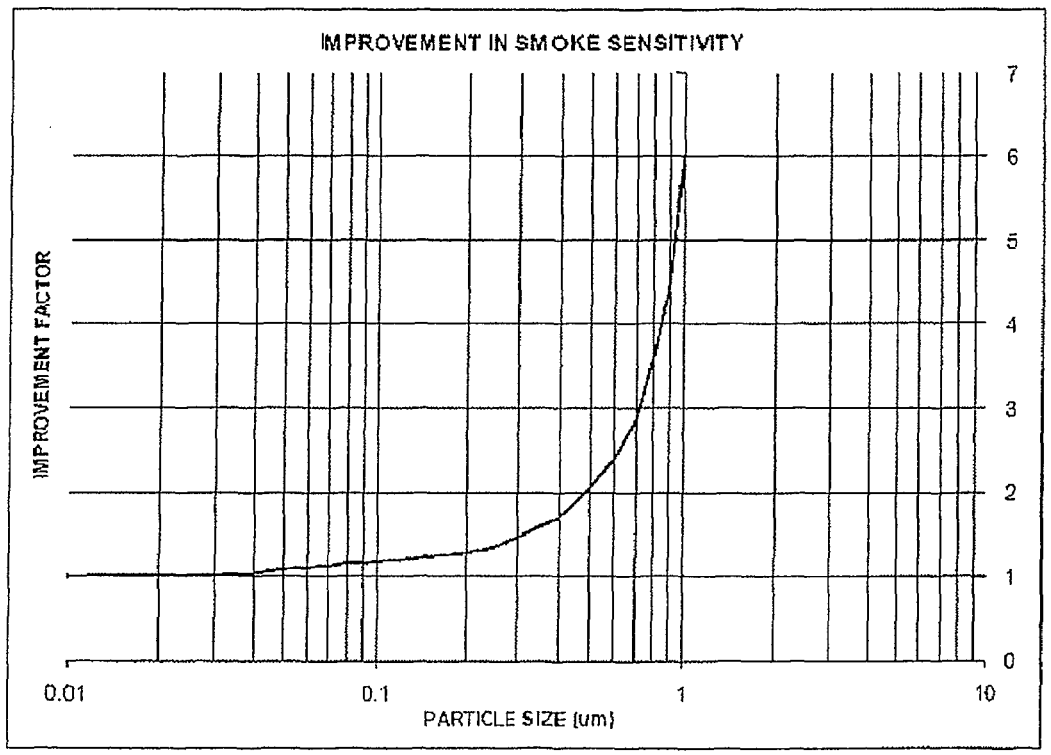
FIG. 4

PARTICLE MONITORS AND METHOD(S) THEREFOR

FIELD OF INVENTION

The present invention relates to the field of the detection, analysis and/or determination of matter or particles suspended in fluid.

In one particular form, the present invention relates to smoke detectors, which detect unwanted pyrolysis or combustion of material. In another form, the present invention relates to smoke detectors of the early detection type, and which may be applied to ventilation, air-conditioning or duct monitoring of a particular area. In yet another form, the present invention relates to surveillance monitoring, such as building, fire or security monitoring. In still another form, the present invention relates to environment monitoring, such as monitoring, detection and/or analysis of a fluid, zone, area and/or ambient environment, including commercial and industrial environments.

As will become apparent, the present invention has broad application and thus the particular forms noted above are only given by way of example, and the scope of the present invention should not be limited to only these forms.

BACKGROUND ART

The present inventor has determined an understanding that the type of smoke produced in various pyrolysis and combustion circumstances is different. Fast flaming fires tend to produce a very large number of very small solid particles which may agglomerate into random shapes to form soot. In contrast, the early stages of pyrolysis tend to produce a much smaller number of relatively large liquid particles (of high boiling point), typically existing as aerosols that may agglomerate to form larger, translucent spheres.

The present inventor has also determined an understanding that the detection of relatively large particles which slowly increase in quantity over an extended period of time would typically indicate a pyrolysis or smoldering condition, whereas the detection of numerous small particles arising quickly and without earlier pyrolysis or smoldering could indicate arson involving the use of accelerants.

The present inventor has also determined an understanding that dust particles are generated by the abrasion or non-thermal decomposition of natural materials or organisms in the environment and that such particles are in general very large compared with smoke particles.

The present inventor has also determined and understanding of the following:

Conventional point type smoke detectors are primarily designed for ceiling installation in a protected area. These detectors have relatively low sensitivity and have difficulty in detecting the presence of unwanted pyrolysis where large volumes of air pass through the area being monitored, thus diluting the ability for the detector to sense the presence of unwanted pyrolysis.

To overcome these disadvantages, highly-sensitive aspirated smoke detectors were developed, and are often deployed on ducts for the purpose of monitoring an area. These detectors provide a measure of sensitivity some hundred times greater than convention point detectors. These aspirated systems employ suction pressure via an air pump and also employ a dust filter to reduce unwanted dust pollution from soiling the detector or from being detected indistinguishably from smoke and causing the triggering of a false alarm.

The smoke detector preferably employed in an aspirated system is a nephelometer. This is a detector sensitive to many sizes of particles, such as the many smoke particles produced in fires or during the early stages of overheating, pyrolysis or smoldering.

Optical type smoke (or airborne particle) detectors of the prior art typically use a single light source to illuminate a detection zone that may contain such particles. The use of two light sources has been proposed for some detectors. A proportion of this light may be scattered off the particles toward a one or more receiver cells (or sensors). The output signal(s) from the receiver cell(s) is used to trigger an alarm signal.

Other detectors use a laser beam, providing a polarized monochromatic light source, typically in the near infrared wavelength. These detectors, however, are not considered to be true nephelometers as they are prone to being overly sensitive to a particular particle size range at the expense of other size ranges.

The disadvantage suffered by the above detectors is their relative insensitivity to very small particles characteristic of early pyrolysis and incipient fires, as well as certain fast flaming fires.

Ionization smoke detectors, on the other hand, utilize a radioactive element such as Americium, to ionize the air within the detection chamber. These detectors are relatively sensitive to very small particles produced in flaming fires, but relatively insensitive to larger particles produced in pyrolysis or smoldering. They have also been found relatively prone to draughts, which serve to displace the ionized air within the detection chamber and thus trigger a false alarm. This places a practical limit on their useful sensitivity.

Other smoke detectors have used a Xenon lamp as a single light source. The Xenon lamp produces a continuous spectrum of light similar to sunlight, embracing ultraviolet, visible and infrared wavelengths. Use of this light source can detect all sized of particles and the detectors produce a signal that is proportional to the mass density of the smoke, which is characteristic of a true nephelometer. However, the type of fire cannot be characterized because the particular particle size cannot be discerned. The Xenon light also has only a relatively short life-span of some 4 years and its light intensity is known to vary, which affects the sensitivity.

The present inventor has also realized that in order to provide a wide output range in sensitivity, prior art detectors provide an analog to digital converter (ADC) used to apply the smoke level data to a microprocessor. With careful design, substantially all of the capacity of the ADC is used to represent the maximum smoke levels, such as (typically) 20%/m. ADC's operating at 8-bit resolution are useful, whereas a 10-bit or larger ADC's are more expensive and require larger microprocessors. A 10-bit ADC has been found to allow this 20%/level to e divided into 1024 steps, each step representing an increment of 20/1024=0.02%/m. So the steps are 0, 0.02, 0.04, 0.06, etc, with no opportunity for finer increments. At low smoke levels this is considered a very coarse resolution, making it difficult to set alarm thresholds finely. However at high smoke levels, a resolution of 0.02%/m is unnecessary—the ability to set an alarm threshold at 10.00%/m or 10.002%/m for example, has little if any benefit. So the resolution of the prior art detectors is considered too coarse at low smoke levels and too fine at high smoke levels.

Any discussion of documents, devices, acts or knowledge in this specification is included to explain the context of the invention. It should not be taken as an admission that any of the material forms a part of the prior art base or the common general knowledge in the relevant art in Australia or elsewhere on or before the priority date of the disclosure and claims herein.

An object of the present invention is to provide a particle detection apparatus and method(s) which enable an improved detection, discrimination and/or analysis of particles, pyrolysis, smoldering and/or flaming events and dust, thus providing a corresponding improvement in fluid-borne particle detection.

A further object of the present invention is to provide a particle detection apparatus and method(s) suitable for use with ducts or as a stand-alone detector and/or monitor.

A still further object of the present invention is to alleviate at least one disadvantage associated with the prior art.

SUMMARY OF INVENTION

In accordance with aspects of the present invention, the monitoring, surveillance, determination, detection and/or analysis or particles, environment, fluid, smoke, zone or area may comprise determination of the presence and/or characteristic(s) of the particles as is required given the particular application of the present invention.

In this regard, an aspect of invention provides, a method of and/or device for determining, in a fluid sample, the presence of particle(s) having substantially a predetermined size or range of size(s), comprising the steps of illuminating the sample with a first wavelength of light, obtaining a first responds signal indicative of the first illumination, illuminating the sample with a second wavelength of light, obtaining a second responds signal indicative of the second illumination, and providing a predetermined threshold for comparison of the first and second signals.

In accordance with another aspect of invention, there is provided a method of and/or device or control apparatus for adjusting the sensitivity of a particle detector which is adapted to illuminate a sample with a first and a second illumination, comprising the step of determining the presence of the particles having a predetermined size or range of size(s) by comparing signals indicative of the first and second illuminations, the comparison being adjusted in accordance with a threshold.

Preferably, the comparison is truncated at the threshold. Preferably the threshold is a predetermined ratio of the first and second illuminations.

A further of invention is provided, namely a method of and/or device or control apparatus for adjusting the sensitivity of a particle detector, comprising the step of adjusting the sensitivity of a particle detector, comprising the step of adjusting the intensity of a light projector such that the magnitude of light scattered from a sample is of a predetermined value.

Preferably, the illuminations are of differing wavelength and/or polarization.

The present invention also provides a monitor for monitoring the presence, concentration and characteristics of particulates in fluid medium.

In essence, the present invention effectively uses the ratio of one light source to another light source, for example the comparative measure of infrared light to the blue light, such that when the infrared light reaches say 90% (or some other predetermined threshold value) of the blue light, which for example represent particles of predominantly say 1 micron diameter, particles larger than this size are then rejected. In other words, the present invention provides a method of and device for detecting particles of many size(s) and rejecting particles larger than a predetermined size (say 1 micron such as dust) by comparing results of illumination of one wavelength with an illumination of another wavelength an applying a threshold to the comparison result.

Thus, the present invention uses a ratio of illumination responses in combination with a subtraction process. The point of discrimination (transition point) may be adjusted by altering this ratio—reducing the percentage, reduces the transition particle size, i.e. the particle acceptance/rejection size—typically in the range 0.5 to 1.1 micron. In other words, the present invention uses the ratio of illumination responses in combination with a comparative process (for example subtraction) in order to determine a rejection threshold. The transition point or rejection threshold applicable to a certain application maybe determined through experimentation as the response to illumination (as disclosed herein by graphs) is not perfect in practice because the graphs are not smooth as shown, and the smoothness depends on the polydispersity (size homogeneity) of the particles. The more mono-disperse the particles, the less smooth are the curves.

A feature of the present invention is its adaptability to particular environments. It has been found that the present invention can avoid unwanted alarms from, for example, incinerator ash which for at least one industrial process, produces particles perhaps as small as 0.8 micron. The adjustable transition point enables these particles to be rejected as dust by the detector.

It has also been found that there is a need to detect aged smoke, especially smoke composed of high melting-point droplets that have coalesced into particles that may be 0.7 microns or larger. Automatic discrimination may be used to maintain relatively high sensitivity to these particles, while also retaining the ability to reject dust. It has been found that to produce a product that responds to this aged droplet smoke yet rejects fine ash is uniquely able to be addressed by the present invention.

Preferably, different wavelengths, various ranges of wavelengths and/or polarization are used to detect predetermined particles in fluid. Furthermore, preferably, subtraction or providing a ratio of two signals enables a more measureable output indicating the detection of particles and the particle sizes.

Other aspects and preferred aspects are disclosed in the specification and/or defined in the appended claims, forming a part of the description of the invention.

The present invention has been found to result in a number of advantages, such as:
The ability to maintain relatively high sensitivity to aerosol particles up to a predetermined size and/or predetermined range of size(s),
Improved very early warning of an incipient fire by virtue of particle size and/or a range of particle size(s) discrimination,
The ability to selectively reject and/or reject in accordance with a predetermined basis selected size particles and/or range of particle size(s) that may otherwise be more-likely to be considered to cause unwanted detections.
The present invention has numerous applications, including, without limitation, surveillance monitoring, such as building, fire or security monitoring and environment monitoring, such as monitoring, detection and/or analysis of a fluid, zone, area and/or ambient environment, including commercial and industrial environments.

Throughout this specification, reference is made to a number of different light sources having certain wavelengths. Reference to the light sources and wavelengths is made only as they are current commercially available light sources. It is to be understood that the principle underlying the present invention have equal applicability to light sources of different wavelength(s).

A monitor may include reference to a detector or similar apparatus.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Further disclosure, objects, advantages and aspects of the present application may be better understood by those skilled in the relevant art by reference to the following description of preferred embodiments taken in conjunction with the accompanying drawings, which are given by way of illustration only, and thus are not limitative of the present invention, and in which:

FIG. 3 illustrates the threshold feature of the present invention, and FIG. 4 illustrates a representation of an improvement attained by application of the present invention.

DETAILED DESCRIPTION

In the embodiment described, at least two channels are referred to, one being channel A, which uses wavelengths such as red or infrared wavelengths, the other being channel B, which uses wavelengths such as blue wavelengths. Additional channels could be employed such as channel C, which uses wavelengths such as green wavelengths. Other wavelengths may also be employed in accordance with the present invention, as will become apparent in the following description. Generally it is preferred if a reading established from a longer wavelength is compared with a reading establish from a shorter wavelength. Most preferably, the longer wavelength reading is subtracted from the shorter wavelength reading. A ratio may also be used to compare wavelength readings. The present invention has application to smoke and/or particle detectors as disclosed in WO2001059737 and WO2005043479,the disclosure of which is herein incorporated by reference. It is to be noted, however, that the present invention has application, not only to those detectors, but to smoke and/or particle detectors in general.

Discrimination

Figure 1:
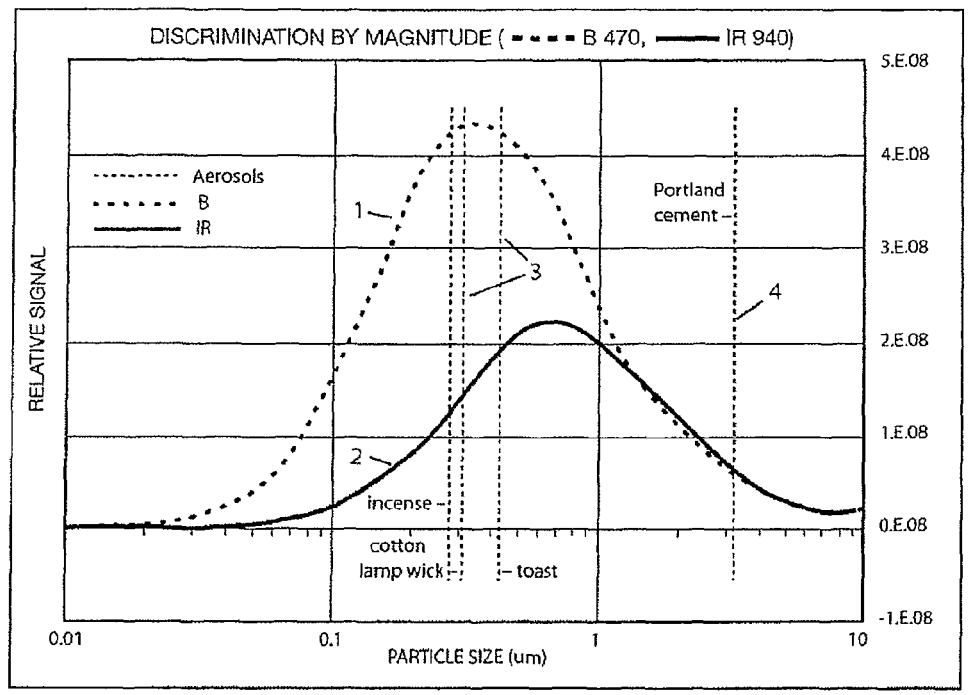
FIG. 1 illustrates the magnitude of light that is scattered off particles of various sizes.

Two light projectors are used alternately to illuminate a cloud of airborne particles (an aerosol). Based on the light scattering theory of Gustav Mie, the magnitude of light scattered off the particles and received by a receiver has been calculated. Calculations are performed to represent various, if not all, particle sizes within the range of 0.01 micron to 10 micron, although dust particles may extend to as large as 100 micron. It is known that smoke particles are predominantly smaller than 1 micron, whereas dust particles are predominately larger than 1 micron. By way of background, it has been determined by the present inventor that the wavelengths of light employed have an important bearing the sensitivity of the present device to particle sizes. The scattering of light from particles over various size ranges has been described in 'Absorption and Scattering of Light by Small Particles' by Bohren C F and Huffman D R, ISBN 0-471-05772-X.

It has been determined that Mie equations are appropriate for considering particles of a size range appropriate to common smoke and dust. Fast flaming fires tend to produce a very large number of very small carbonaceous particles which may agglomerate into random shapes to form soot. In contrast, the early stages of pyrolysis tend to produce a much smaller number of relatively larger liquid particles (of high boiling point), typically existing as aerosols that may agglomerate to form even larger, translucent spheres or droplets. Dust particles generally result from mechanical abrasion and have random shapes that can be approximated as yet larger spheres for modeling purposes. A source of smoke or dust is unlikely to be mono-disperse (contain one particle size), but is more-likely poly-disperse, with a size range and concentration that may follow a Gaussian distribution. It has been found by the inventor that a typical standard deviation for the size distribution is in the vicinity of 1.8 to 2.

It has also been realized by the present inventor that airborne particle distributions in cities are bimodal, peaking at round 0.1 micron and 10 micron. Typically, smoke particles lie in the range of 0.01 to 1 micron, whereas airborne dust particles lie in the range of 1 to 100 micron. However there is some overlap at the 1 micron boundary because the smallest dust particles in nature are smaller than the largest possible smoke particles.

The present inventor has also determined that certain particle sizes are more easily discerned by particular (different) wavelengths of light. Given this, we use two wavelengths of incident light. Commercially available sources of light can range anywhere, for example, from blue to infrared such as light ranging from 400 nm wavelength (blue) to 1050 nm wavelength (infrared). For example, 470 nm (blue) and 940 nm (infrared) could be used.

By application of Mie theory to particle sizes ranging from 0.01 to 10 micron mass mean diameter and using a standard deviation of 1.8,it can be determined that blue light is quite suitable for the detection of smoke and dust, whereas infrared light is at least equally suitable for the detection of dust but is comparatively poor at detecting a wide range of smoke particles due to the lack of response to small particles. Various combinations of wavelengths and lighting effects may also be used as disclosed in the application incorporated herein by reference.

FIG. 1 illustrates the magnitude of light that is scattered off these particles at various particle sizes. Note that the graphs of the figures have been smoothed for greater clarity. The blue curve 1 shows the relative magnitude of light scattered by, for example, blue light (470 nm). The red curve 2 shows the relative magnitude of light scattered by, for example, infrared light (940 nm).

In another aspect of invention, the intensity of the light projectors is preferably adjusted so that, for particles larger than about 1 micron, the magnitude of scattered light is virtually the same, whether blue or infrared light is used. The intensity may either be factory set (permanent), present (before detection) or self-adjusting according to particles being detected. For particles smaller than 1 micron, the magnitude of scattered light is very different.

As points of reference, FIG. 1 also illustrates aerosols 3 representing the average particle size for smoke, for example incense, cotton, lamp wick and toast fuels, while the average particle size of dust is represented by aerosol 4, for example Portland cement.

These magnitudes of scattered light may be received by a photocell of a detector to generate signals that are proportional to the light intensity, substantially as they appear in FIG. 1. It can be seen that for infrared light 2, the relative signal magnitude obtained for smoke (especially incense) and dust would be similar. For blue light 1 the relative signal magnitude would be substantially greater for smoke, than it would be for dust.

Figure 2:
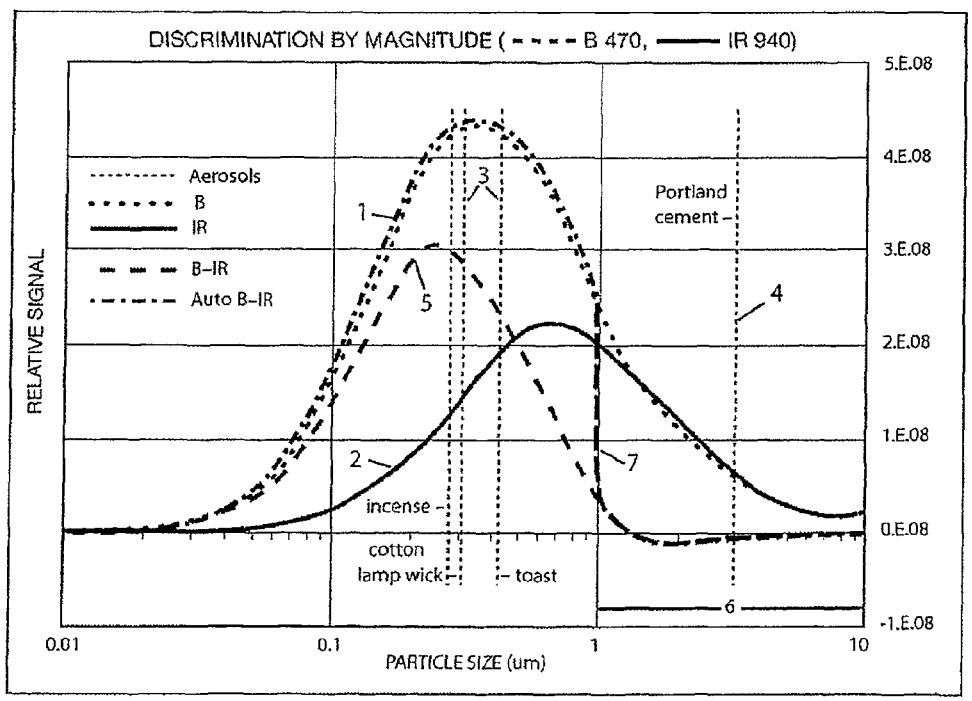
FIG. 2 illustrates a resultant signal obtained from a subtraction process.

FIG. 2 shows the result (brown) of subtracting the signal obtained for infrared light, from the signal obtained for blue light. This aspect of invention is disclosed in co-pending application WO2005043479,also by the present inventor. From FIG. 2, it can be seen subtracting the red signal 2 from the blue signal 1 results in a subtracted signal 5. The resulting subtracted signal 5 has substantially nil or slightly negative responds to large particles such as dust, while retaining a substantial response to small particles such as smoke. This enables a smoke detector (for fire alarms) to be designed, to discriminate against dust so that it is relatively resistant or tolerant to false alarms caused by dust.

The inventor has realized that in comparing the blue curve 1 with the subtracted curve 5, the sensitivity of a smoke detector to smoke can require enhancement in the discrimination process, because the infrared signal 2 extends into the smoke region 6.

In another aspect of invention, the present inventor has realized that it is possible to enhance the discrimination process, and result in greater detector sensitivity by predicating the subtraction of signals on a relative threshold level. For example, in FIG. 2, the subtraction of the infrared signal 2 from the blue signal 1 may be conditional upon the infrared signal 2 being at least 80% of the blue signal 1. From FIG. 2 we see that this occurs at about 1 micron particle size. The result is illustrated in FIG. 3. In a preferred embodiment, the relative threshold level feature is automatically selected.

In applying this threshold level feature in FIG. 2, a solution can be found where there is relatively high sensitivity to smoke, especially smoke particles larger than 0.5 micron, as well as dust rejection. This is indicated in FIG. 2 as a curve (pale blue) 7 whereby the discrimination process comes into effect only for particles larger than 1 micron. In this way, discrimination of dust 4 occurs only for large particles, so that the sensitivity to smoke particles 3 (especially in the range of 0.5 to 1 micron) is substantially not reduced.

By adjustment of the threshold above or below the 85% value mentioned, the particle size at which discrimination comes into effect, may also be adjusted. In a preferred embodiment a suitable range of threshold adjustments is from about 60% to 95%, however, the threshold level may be made at any value depending on the application of the device to which the present invention is applied.

FIG. 3 emphasizes the advantage of automatic discrimination (pale blue) 7 compared with full discrimination curve 5. The sensitivity of the smoke detector to smoke particles in the range 0.5 to 1 micron is especially improved, without substantially compromising the rejection of dust 4.

FIG. 4 represents the advantage of automatic discrimination expressed as a factor when comparing (from FIG. 3) curve 1 with curve 5. Again referring to FIG. 3, at about 0.5 micron the curve 1 is about twice the magnitude of curve 2, so the improvement is a factor of two. Looking at about 1 micron, curve 1 approaches six times the magnitude of curve 5. Repeating this process at other wavelengths provides the representation illustrated in FIG. 4, whereby it can be seen that the improvement for smoke particles larger than 0.5 micron is at least a factor of 2,rising to a maximum of 6.

The signals derived indicating the presence of particles may be processed as disclosed in the applications referred to above, and/or in accordance with processes know to those skilled in the art.

While this invention has been described in connection with specific embodiments thereof, it will be understood that it is capable of further modification(s). This application is intended to cover any variations uses or adaptations of the invention following in general, the principles of the invention and including such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. Various modifications and equivalent arrangements are intended to be included within the spirit and scope of the invention and appended claims. Therefore, the specific embodiments are to be understood to be illustrative of the many ways in which the principles of the present invention may be practiced. In the following claims, means-plus-function clauses are intended to cover structures as performing the defined function and not only structural equivalents, but also equivalent structures. For example, although a nail and a screw may not be structural equivalents in that a nail employs a cylindrical surface to secure wooden parts together, whereas a screw employs a helical surface to secure wooden parts together, in the environment of fastening wooden parts, a nail and a screw are equivalent structures.

"Comprises/comprising" when used in this specification is taken to specify the presence of stated features, integers, steps or components but does not preclude the presence or addition of one or more other features, integers, steps, components or groups thereof.

The claims defining the invention are as follows:

1. A particle detector for determining a presence of particles in a fluid sample, the detector comprising:
   a first light source configured to illuminate the sample in a first illumination with light of a first wavelength;
   a second light source configured to illuminate the sample in a second illumination with light of a second wavelength;
   sensor means configured to obtain a first response signal indicative of the first illumination from light scattered off of particles in the sample and to obtain a second response signal indicative of the second illumination from light scattered off of particles in the sample; and
   logic means configured to receive the first and second signals and to provide a predetermined threshold for comparison of the first and second signals, the threshold being a predetermined ratio of signals indicative of the first and second illuminations, said logic means being configured for basing the comparison upon a subtraction of the first signal from the second signal.

2. The particle detector according to claim 1, wherein said logic means are configured to adjust the predetermined threshold.

3. The particle detector according to claim 1, wherein said logic means are configured to adjust the predetermined threshold in response to a plurality of first and second illuminations.

4. The particle detector according to claim 1, wherein said logic means are configured to truncate the comparison at the threshold.

5. The particle detector according to claim 4, wherein the ratio is substantially in the range of 60 to 95%.

6. The particle detector according to claim 1 configured to:
illuminate the sample in a first illumination with light of the first wavelength, and obtain a first response signal indicative of the first illumination;
illuminate the sample in a second illumination with light of the second wavelength, and obtain a second response signal indicative of the second illumination; and
provide a threshold for comparison of the first and second signals, compare the first and second signals, and determine therefrom a presence of particles having a predetermined size or range of sizes in the fluid sample.

7. The particle detector according to claim 6 wherein the size or range of sizes of particles is substantially in a range of 0.01 to 100 micron.

8. The particle detector according to claim 7 wherein the size or range of sizes of particles is substantially in a range of 0.5 to 1.0 micron.

9. The particle detector according to claim 1, wherein the threshold is a predetermined ratio of the first and second illuminations.

10. The particle detector according to claim 1, wherein said logic means, upon detecting particles of a predetermined size or range of sizes, are configured to output an alarm signal for triggering an alarm.

11. The particle detector according to claim 10, wherein the alarm signal is indicative of at least one alarm condition selected from the group consisting of pyrolysis, smoldering, and smoke event.

12. The particle detector according to claim 1, wherein said first light source is configured to illuminate with infrared light and said second light source is configured to illuminate with visible blue light.

13. The particle detector according to claim 1, configured to:
illuminate the sample with at least one further wavelength of light, in which particles of at least one further size or range of sizes are relatively responsive to the further wavelength of light;
obtain at least one further response signals indicative of the further illumination; and
provide a predetermined threshold for comparison of the first, second, and/or further signals.

14. The particle detector according to claim 1, which comprises polarizing at least one of the illuminations.

15. The particle detector according to claim 1 wherein the first illumination is in the range of 650 nm to 1050 nm, and the second illumination is in the range of 400 nm to 500 nm.

16. A particle detector for determining a presence of particles in a fluid sample, the detector comprising:
a first light source configured to illuminate the sample in a first illumination with light of a first wavelength, the first illumination being adjusted for providing a response for particle sizes substantially not of the size or outside the predetermined range;
a second light source configured to illuminate the sample in a second illumination with light of a second wavelength the second illumination being adjusted for providing a response from particle sizes both substantially of the size or within the predetermined range and particle sizes substantially not of the size or outside the predetermined range;
sensor means configured to obtain a first response signal indicative of the first illumination and to obtain a second response signal indicative of the second illumination; and
logic means configured to receive the first and second signals and to provide a predetermined threshold for comparison of the first and second signals.

17. A method of adjusting a sensitivity of a particle detector, the method which comprises:
providing a particle detector according to claim 1; and
adjusting an intensity of a light projector such that a magnitude of light scattered from a sample is of a predetermined value.

18. The particle detector according to claim 17, wherein the intensity of the light projector is adjusted according to light impinging upon a sensor.

19. The particle detector according to claim 18, which comprises adjusting such that a magnitude of light scattered from the first and second illuminations is substantially the same for a particles of substantially 1 micron or larger in size.

* * * * *